(12) United States Patent
Von Hagen

(10) Patent No.: US 9,994,810 B2
(45) Date of Patent: Jun. 12, 2018

(54) PROCESS FOR PRODUCING CELL CULTURE MEDIA

(71) Applicant: Merck Patent GmbH, Darmstadt (DE)

(72) Inventor: Joerg Von Hagen, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 69 days.

(21) Appl. No.: 14/406,879

(22) PCT Filed: May 17, 2013

(86) PCT No.: PCT/EP2013/001486
§ 371 (c)(1),
(2) Date: Dec. 10, 2014

(87) PCT Pub. No.: WO2013/185876
PCT Pub. Date: Dec. 19, 2013

(65) Prior Publication Data
US 2015/0166949 A1 Jun. 18, 2015

(30) Foreign Application Priority Data
Jun. 15, 2012 (EP) .................................... 12004517

(51) Int. Cl.
*C12N 5/00* (2006.01)
*B02C 23/00* (2006.01)
*A61K 9/14* (2006.01)
*A61K 9/19* (2006.01)

(52) U.S. Cl.
CPC ............ *C12N 5/0018* (2013.01); *B02C 23/00* (2013.01); *A61K 9/141* (2013.01); *A61K 9/19* (2013.01); *C12N 2500/05* (2013.01); *C12N 2500/10* (2013.01)

(58) Field of Classification Search
CPC ......... C12N 5/0018; A61K 9/19; A61K 9/141
USPC .................... 435/404, 405, 406, 407, 408
See application file for complete search history.

(56) References Cited

U.S. PATENT DOCUMENTS

| | | | |
|---|---|---|---|
| 6,159,724 A | 12/2000 | Ehret | |
| 6,383,810 B2 | 5/2002 | Fike et al. | |
| 7,572,632 B2 | 8/2009 | Fike et al. | |
| 2001/0049141 A1 | 12/2001 | Fike et al. | |
| 2003/0153079 A1 | 8/2003 | Fike et al. | |
| 2004/0087022 A1 | 5/2004 | Fike et al. | |
| 2006/0270038 A1 | 11/2006 | Fike et al. | |
| 2006/0275886 A1 | 12/2006 | Fike et al. | |
| 2008/0019883 A1 | 1/2008 | Fike et al. | |
| 2008/0261308 A1 | 10/2008 | Fike et al. | |
| 2008/0311660 A1 | 12/2008 | Fike et al. | |
| 2011/0129926 A1 | 6/2011 | Fike et al. | |
| 2011/0306129 A1* | 12/2011 | Nistor ................. | C12N 5/0018 435/366 |
| 2012/0276630 A1 | 11/2012 | Fike et al. | |
| 2013/0065300 A1 | 3/2013 | Fike et al. | |
| 2013/0109094 A1 | 5/2013 | Fike et al. | |
| 2013/0112786 A1* | 5/2013 | Bausch ................. | B02C 19/186 241/15 |

FOREIGN PATENT DOCUMENTS

| | | |
|---|---|---|
| CN | 1099797 A | 3/1995 |
| EP | 01/55427 A1 | 9/1985 |
| EP | 06/84307 A1 | 11/1995 |
| JP | S57-050884 A | 3/1982 |
| JP | 2005-037522 A | 2/2005 |
| JP | 2011239794 A | 12/2011 |
| WO | 98/36051 A1 | 8/1998 |
| WO | 02/36735 A2 | 5/2002 |
| WO | 03/048313 A2 | 6/2003 |
| WO | 2007-111210 A1 | 4/2007 |

OTHER PUBLICATIONS

International Search Report from PCT/EP2013/001486 dated Jun. 20, 2013.
Richard Fike et al. "Advanced Granulation Technology (AGTtm)" Cytotechnology, [2001], vol. 36, pp. 33-39.
David W. Jayme et al. "Development of Serum-Free Media: Optimization of Nutrient Composition and Delivery Format" Cell Biology, [2006], pp. 33-41.
Frank B. Young et al. "Preparation and Use of Dry Powder Tissue Culture Media" General Biochemicals, [1966], pp. 108-110.
Chun Fang Shen et al. "Micro-quantitation of lipids in serum-free cell culture media: a critical aspect is the minimization of interference from medium components and chemical reagents" Journal of Chromatography B., [2004], vol. 810, pp. 119-127.
Scott J. Jacobia et al. "Trace Element Optimization Enhances Performance and Reproducibility of Serum-Free Medium" Animal Cell Technology: Basic and Applied Aspects, [2006], pp. 193-199.
D. Jayme "Development and Optimization of Serum-free and Protein-free Media" Medicines from Animal Cell Culture, [2007], pp. 29-44.
Japanese Examination Report for corresponding Japanese Application No. 2015-56500; dated Feb. 28, 2017.
Product Information Dulbecco's Modified Eagle's Medium/High Modified with 4500 mg/L dextrose, with 4.0 mM L-glutamine, without sodium pyruvate, Catalog No. 51441C, SAFC Biosciences Accelerate Success, dated Dec. 2006, 2 pages.
English language Abstract for Japanese Patent Laid-Open No. 2011-239794; published Dec. 1, 2011.
English language Abstract for Japanese Patent Laid-Open No. S57-050884; published Mar. 25, 1982.
Partial English translation of WO2007/111210; published Apr. 10, 2007.
English language Abstract for Japanese Patent Laid-Open No. 2005-375222; published Feb. 10, 2005.

* cited by examiner

*Primary Examiner* — Kara Johnson
(74) *Attorney, Agent, or Firm* — Millen, White, Zelano & Branigan, P.C.

(57) ABSTRACT

The present invention relates to an a process for manufacturing dry powder cell culture media. The preparation and usage of mixed particles generated by co-lyophilisation leads to homogenously blended cell culture media.

6 Claims, 3 Drawing Sheets

PROCESS FOR PRODUCING CELL CULTURE MEDIA

The present invention relates to an a process for manufacturing dry powder cell culture media. The preparation and usage of mixed particles generated by co-lyophilisation leads to homogenously blended cell culture media.

BACKGROUND OF THE INVENTION

Cell culture media in aqueous solution can provide an environment which supports and maintains the growth of cells and/or maintains a desired physiological cellular condition adventitious to the targeted production of certain products.

Cell culture media comprise of a complex mixture of components, sometimes more than one hundred different components, depending on the type of organism whose growth and/or targeted physiological status shall be supported.

The cell culture media required for the propagation of mammalian, insect or plant cells are typically much more complex than the media to support the growth of bacteria, yeast or fungi.

The first cell culture media that were developed consisted of undefined components, such as plasma, serum, embryo extracts, or other non-defined biological extracts or peptones. A major advance was thus made with the development of chemically defined media. Chemically defined media often comprise but are not exclusively limited to amino acids, vitamins, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying cells with a substantial nutrient base for growth and/or production of biopharmaceuticals from same said cells.

The production of cell culture media in the form of powders is very critical. Powdered media are typically produced by admixing the dried components of the culture medium via a mixing and milling process, e.g., ball-milling.

In milling processes on the other hand it is often difficult to generate homogenous mixtures as the ingredients with up to 9 orders of magnitude difference in concentration need to be homogenized. That means components of which less than a microgram is present in one kilogram of a media composition need to be homogenously distributed in the cell culture medium.

It has been tried to overcome those difficulties by lyophilizing a pre-made liquid culture medium. However, in a lyophilisation process some of the components of the medium might become insoluble or aggregate upon lyophilization such that resolubilization is difficult or impossible. Additionally, many of the media supplements, particularly serum supplements such as FBS, show a substantial loss of activity or are rendered completely inactive if attempts are made to produce powdered supplements by processes such as lyophilization.

Consequently, there exists a clear need for finding an improved process for manufacturing powdered cell culture media that do not have the disadvantages mentioned above.

BRIEF DESCRIPTION OF THE INVENTION

It has been found that powdered cell culture media with a homogenous distribution of especially the components that are present in low quantities can be produced. This is achieved by preparing mixed particles of at least one low abundant component and one carrier component which is present in the medium in higher concentration. Those mixed particles are prepared by co-lyophilisation and can then be added to the mixture of components that is subjected to milling.

The present invention is thus directed to a process for manufacturing cell culture media by a) co-lyophilizing at least two components of the cell culture medium b) mixing the one or more co-lyophilisates generated in step a) with the other components of the cell culture medium c) subjecting the mixture of step b) to milling In a preferred embodiment, in step a) the amount of one component, the low-abundant component, is less than 5% (by weight) of the amount of the other component, the high abundant component. That means if 100 g of the high abundant component is used, less than 5 g of the low abundant component is used.

In a preferred embodiment, the high abundant component is Sodium Chloride (NaCl), Potassium chloride (KCl), Calcium chloride ($CaCl_2$), Magnesium sulphate ($MgSO_4$) or Magnesium chloride ($MgCl_2$).

In another preferred embodiment in step a) the co-lyophilisation is performed by generating an aqueous solution of the components, freezing the mixture and removing the liquid under reduced pressure.

In another preferred embodiment, the mixture from step b) is milled in a pin mill, fitz mill or a jet mill.

In another preferred embodiment, the mixture from step b) is cooled to a temperature below 0° C. prior to milling.

In another embodiment, in step a) two or more different co-lyophilisates are produced, each by co-lyophilizing at least two components of the cell culture medium.

The present invention is further directed to powdered cell culture media produced by the method according to the present invention.

The present invention is further directed to powdered cell culture media comprising one or more co-lyophilisates.

In a preferred embodiment, the powdered cell culture media comprise two or more co-lyophilisates.

In a preferred embodiment, in at least one co-lyophilisate the amount of at least one component is less than 1% of the amount of at least one other component.

In another preferred embodiment, at least one co-lyophilisate comprises Sodium Chloride (NaCl), Potassium chloride (KCl), Calcium chloride ($CaCl_2$), Magnesium chloride ($MgCl_2$) or Magnesium sulphate ($MgSO_4$).

Figure 1:
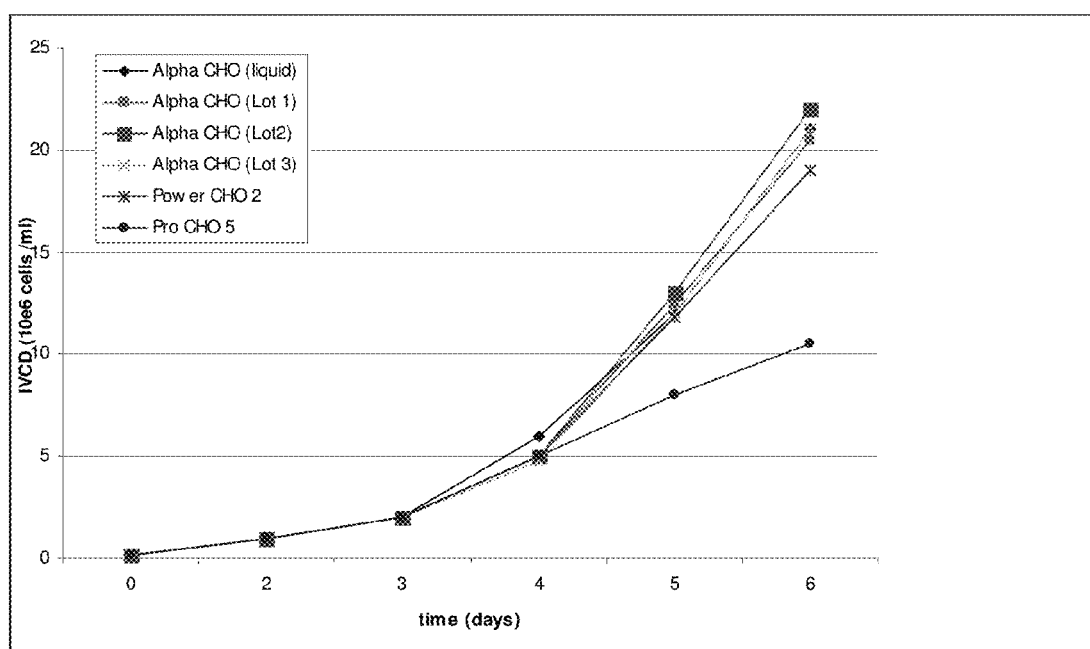
FIG. 1—Is a graph.

A cell culture medium according to the present invention is any mixture of components which maintains and/or supports the in vitro growth of cells and/or supports a particular physiological state. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells, media supplements or feeds. In a preferred embodiment the cell culture medium is a full medium.

Typically, the cell culture media according to the invention are used to maintain and/or support the growth of cells in a bioreactor and/or to support a particular physiological state.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins to the media. Chemically undefined or poorly defined chemical components are those whose chemical composition and structure is not known, are present in varying composition or could only be defined with enormous experimental effort—comparable to the evaluation of the chemical composition and structure of a protein like albumin or casein.

A powdered cell culture medium is a cell culture medium resulting from a milling process. That means the powdered cell culture medium is a dry, particulate medium—not a liquid medium.

Cells to be cultured with the media according to the present invention may be prokaryotic cells like bacterial cells or eukaryotic cells like plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

The size of a particle means the mean diameter of the particle. The particle diameter is determined by laser light scattering in silicone oil.

Lyophilisation according to the present invention is freeze-drying by freezing the material and then reducing the surrounding pressure to allow the frozen water in the material to sublimate directly from the solid phase to the gas phase.

As used herein, "co-lyophilised" or "co-lyophilisate" refers to a product resulting from the lyophilization, freeze-drying, or vacuum drying of more than one compound in solution in the same vessel. For example, two solutions might be combined in the same vessel and the resulting combination of solutions is lyophilized together, thereby lyophilizing the components in the solutions simultaneously. Alternatively, two or more compounds, also called media components, can be dissolved in the same liquid and afterwards be lyophilised together. The resulting product of such a co-lyophilisation is a co-lyophilisate consisting of solid material that comprises a mixture of all components that have been co-lyophilised.

An inert atmosphere is generated by filling the respective container or apparatus with an inert gas. Suitable inert gases are noble gases like argon or preferably nitrogen. These inert gases are non-reactive and prevent undesirable chemical reactions from taking place. In the process according to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy. Pin mills are for example sold by Munson Machinery (USA), Premium Pulman (India) or Sturtevant (USA).

A jet mill uses compressed gas to accelerate the particles, causing them to impact against each other in the process chamber. Jet mills are e.g. sold by Sturtevant (USA) or PMT (Austria).

A fitz mill commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture media which are manufactured according to the method of the present invention typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, fatty acids and/or fatty acid derivatives and/or pluronic acid and/or surface active components like chemically prepared non-ionic surfactants. One example of a suitable non-ionic surfactant are difunctional block copolymer surfactants terminating in primary hydroxyl groups also called poloxamers, e.g. available under the trade name Pluronic® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are the proteinogenic amino acids, especially the essential amino acids, leucine, isoleucine, lysine, methionine, phenylalanine, threonine, tryptophane and valine, as well as the non-proteinogenic amino acids like D-amino acids.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are Copper(II) sulphate pentahydrate ($CuSO_4.5H_2O$), Sodium Chloride (NaCl), Calcium chloride ($CaCl_2.2H_2O$), Potassium chloride (KCl), Iron(II)sulphate, sodium phosphate monobasic anhydrous ($NaH_2PO_4$), Magnesium sulphate anhydrous ($MgSO_4$), sodium phosphate dibasic anhydrous ($Na_2HPO_4$), Magnesium chloride hexahydrate ($MgCl_2 \cdot 6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, heme nucleotide phophates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

Freezing according to the present invention means cooling to a temperature below 0° C.

The gist of the present invention is to provide powdered cell culture media by milling. Milling is a very simple and reliable and thus favourable way to produce powdered cell culture media. Up to now a major drawback of milling was an inefficient distribution of low-abundant components. On can easily understand that a low-abundant component of which only one tiny crystal is added to a mixture of one kilogram or more of other components can hardly be homogenously distributed in the milled powdered cell culture medium. The present invention provides an easy and reliable improvement. One or more low-abundant components of the cell culture medium are co-lyophilised with on or more preferably high abundant components of the cell culture medium which work as a carrier. Due to this co-lyophilisation the low-abundant components are homogenously distributed within the resulting solid co-lyophilisate. As most of the mass of the co-lyophilisate is generated by the high-abundant component, it can be added to the cell culture medium in larger amount compared to the pure low-abundant component and can thus be easily measured and is much better homogenously distributed within the resulting medium by milling.

Low-abundant components are those components of which less than 1%, preferably less than 0.1% (weight % in dry powder medium), are present in the powdered cell culture medium.

High abundant components are those components of which more than 5%, preferably more than 10% by weight (weight % in dry powder medium) are present in the powdered cell culture medium.

Examples of low-abundant cell culture media components are known to a person skilled in the art. They may differ depending on the type of cell culture medium. Typical examples are:

Tin or tin salts, manganese or manganese salts, nickel or nickel salts, vanadium or vanadium salts, cadmium or cadmium salts, molybdenum or molybdenum salts, cupper or cupper salts, selenium or selenites, biotin and metasilicate as well as other chemical compounds encompassing one or more of the above mentioned elements. Examples of low-abundant cell culture media components or chemical components comprising a low-abundant cell culture media component are:

Sodium Selenite
Selenious Acid
Barium Acetate
Germanium Dioxide
Potassium Iodide
Silver Nitrate
Zirconyl Chloride $8H_2O$
Aluminum Chloride, $6H_2O$
Ammonium Metavanadate
Ammonium Molybdate, $4H_2O$
Cadmium Chloride, Anhydrous
Chromium Chloride, $6H_2O$
Cobalt Chloride, $6H_2O$
Manganous Sulfate, $H_2O$
Nickel Sulfate, $6H_2O$
Potassium Bromide
Rubidium Chloride
Stannous Chloride, $2H_2O$ A trace element and thus a low-abundant component that is often present in cell culture media according to the present invention is selenium, e.g. in the form of Sodium Selenite or Selenious Acid.

Examples of high-abundant cell culture media components are known to a person skilled in the art. They may differ depending on the type of cell culture medium. Typical examples are:

Glucose and other saccharide components, or salts like Sodium chloride, Potassium chloride, Calcium chloride ($CaCl_2 \cdot 2H_2O$), Magnesium chloride ($MgCl_2$) or Magnesium sulphate ($MgSO_4$). Preferred are salts, especially preferred is sodium chloride.

Co-lyophilisation is preferably performed by co-lyophilising at least one low-abundant component with at least one high-abundant component. In a preferred embodiment, one low-abundant component is co-lyophilised with one high-abundant component.

The amount of the low-abundant component that is subjected to co-lyophilisation is less than the amount of the high abundant component. Preferably, the amount of the low-abundant component is less than 5% of the amount of the high abundant component. That means if 100 g of the high abundant component is used, less than 5 g of the low abundant component is used. As the low abundant component might be present in form of a salt in which only part of the chemical components of the salt is the low abundant component needed for cell growth, the above calculation and the above given amounts relate to the pure mass of the low abundant chemical component needed for cell growth. For example, the component that is used is cadmium sulphate hydrate ($3CdSO_4 \times 8H_2O$) but Cadmium is the low abundant component needed for cell growth. That means the molecular weight of the cadmium sulphate hydrate is 769.51 g/mol while the molecular weight of cadmium is 337.23 g/mol. Consequently one would calculate the amount of low-abundant component needed based on the percentage of cadmium present in said component.

For co-lyophilisation, in a first step, all components to be co-lyophilised are dissolved in a solvent.

The components can be solubilised in one solvent. Alternatively, each component can be dissolved in a separate solvent and the resulting two or more solutions of different components can then be mixed. Typically, all solutions to be mixed have the same solvent.

Suitable solvents are those in which all components are soluble. Examples of suitable solvents are organic solvent or water or mixtures thereof. Preferred is water.

Once the solvent is chosen and the components have been dissolved, the resulting mixture is frozen and lyophilized to dryness. Sometimes an additional solvent is added to the mixture to facilitate lyophilisation. Typically lyophilisation is performed at a temperature below −20° C., preferably at around −80° C. The liquid is typically removed by applying reduced pressure. The resulting co-lyophilisate can also be called mixed particles or mixed solid.

The mixed solid is then preferably milled, e.g. in a ball mill, to generate particles of homogenous size. The resulting particles typically have a particle size below 200 μm. Preferred are particle sizes below 100 μm. Favourable particle sizes are between 15 μm and 100 μm.

The milled co-lyophilisate can then be subjected to trace element quantification to determine the concentration of the low-abundant component in the co-lyophilisate. If necessary, the concentration of the low-abundant component can be reduced by admixing further amounts of the high-abundant component.

The final co-lyophilisate with a defined concentration of the low-abundant component can then be stored or used for the production of cell culture media.

For the latter, a suitable amount of the co-lyophilisate is mixed with the other components of the cell culture medium. It is also possible to generate two or more co-lyophilisates and mix two or more co-lyophilisates with the other components of the cell culture medium. The mixing of the components is known to a person skilled in the art of producing dry powdered cell culture media by milling. Preferably, all components are thoroughly mixed so that all parts of the mixture have nearly the same composition. The higher the uniformity of the composition, the better the quality of the resulting medium with respect to homogenous cell growth.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 μm, most preferably between 25 and 100 μm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules. The medium resulting from milling such dry component is also called dry powdered cell culture medium.

In a preferred embodiment, the milling is performed in an inert atmosphere. Preferred inert protective gas is nitrogen.

In another preferred embodiment, all components of the mixture are freezed prior to milling. The freezing of the ingredients prior to the milling can be done by any means that ensures a cooling of the ingredients to a temperature below 0° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 0° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The freezed mixture is then transferred from the feeder to the mill so that the mixture which is milled in the mill preferably still has a temperature below 0° C., more preferred below −20° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

It has been found that in contrast to other milling processes the process according to the present invention provides homogenous blends even if one or more low-abundant components are present in amounts of less than 1 μg/kg cell culture medium.

The present invention is further directed to a dry cell culture medium comprising at least one co-lyophilisate. Such medium is obtainable by the process according to the present invention.

Typically, the co-lyophilisate is a co-lyophilisate of one low-abundant and one high abundant component.

Preferably, the cell culture medium comprises 1 to 10 different co-lyophilisates.

For use of the milled powdered media a solvent, preferably water (most particularly distilled and/or deionized water or purified water or water for injection) or an aqueous buffer is added to the media and the components are mixed until the medium is totally dissolved in the solvent.

The solvent may also comprise saline, soluble acid or base ions providing a pH range of 1.0-10.0, stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

The present invention is thus further directed to a process for culturing cells by
a) providing a cell culture medium according to the present invention
b) mixing said cell culture medium with water or an aqueous buffer
c) mixing the cells to be cultured with the cell culture medium of step b) in a bioreactor
d) incubating the mixture of step c)

A bioreactor is any container, vessel or tank in which cells can be cultured. Incubation is typically done under suitable conditions like suitable temperature etc. A person skilled in the art is aware of suitable incubation conditions for supporting or maintaining the growth/culturing of cells.

By using the co-lyophilisates for media production the overall amount of the trace elements (low-abundant components) still remains the same as outlined in the recipe, but as the low abundant components are combined with the carrier salt the precision in weighing in a larger amount of substance and the mixing of the low-abundant components is significantly higher.

The present invention is further illustrated by the following figure and example, however, without being restricted thereto.

The entire disclosure of all applications, patents, and publications cited above and below and of corresponding EP application EP 12004517.4, filed Jun. 15, 2012, are hereby incorporated by reference.

EXAMPLES

The following examples represent practical applications of the invention.

1. Preparation of Co-Lyophilisates

| Molybdenum in Ammoniummolybdate × 4H$_2$O | Art. Nr: 201129 |
|---|---|
| (NH$_4$)$_6$Mo$_7$O$_{24}$ × 4H$_2$O | 1235.86 g/mol |
| part of Molybdenum | 671.58 g/mol |
| proportion Molybdän | 54.34% |
| Amount to be co-lyophilised with 100 g NaCl: | |
| Ammoniummolybdat × 4H$_2$O | 85.76 mg |
| part of Molybdenum | 46.60 mg |
| conzentration of Molybdenum in the resulting co-lyophilisate: | 466.03 µg/g |

| Cadmium in Cadmium-sulfate Hydrate | Art. Nr: 201141 |
|---|---|
| 3CdSO$_4$ × 8H$_2$O | 769.51 g/mol |
| part of Cadmium | 337.23 g/mol |
| proprtion of Cadmium | 43.82% |
| Amount to be co-lyophilised with 100 g NaCl | |
| Cadmium-sulfate Hydrate | 53.47 mg |
| part of Cadmium | 23.43 mg |
| conzentration of Cadmium in the resulting co-lyophilisate: | 234.33 µg/g |

| Manganese in Manganesechloride × 4H$_2$O | Art. Nr: 201130 |
|---|---|
| MnCl$_2$ × 4H$_2$O | 197.91 g/mol |
| part of Mangan | 54.94 g/mol |
| proportion of Mangan | 27.76% |
| Amount to be co-lyophilised with 100 g NaCl | |
| Manganesechloride × 4H$_2$O | 27.43 mg |
| part of Manganese | 7.61 mg |
| conzentration Manganese in the resulting co-lyophilisate: | 76.15 µg/g |

| Nickel in Nickel(II)-chloride × 6H$_2$O | Art. Nr: 201142 |
|---|---|
| NiCl$_2$ × 6H$_2$O | 237.66 g/mol |
| part of Nickel | 58.69 g/mol |
| proportion of Nickel | 24.69% |
| Amount to be co-lyophilised with 100 g NaCl | |
| Nickel(II)-chloride × 6H$_2$O | 30.21 mg |
| part of Nickel | 7.46 mg |
| conzentration Nickel in the resulting co-lyophilisate | 74.60 µg/g |

| Silicium in Natriummetasilicat × 5H$_2$O | Art. Nr: 201131 |
|---|---|
| Na$_2$SiO$_3$ × 5H$_2$O | 212.14 g/mol |
| part of Silicium | 28.09 g/mol |
| proportion of Silicium | 13.24% |
| Amount to be co-lyophilised with 100 g NaCl | |
| Natriummetasilicat × 5H$_2$O | 9860.00 mg |
| part of Silicium | 1305.59 mg |
| conzentration Silicium in the resulting co-lyophilisate: | 13055.88 µg/g |

| Vanadium in Sodium Metavanadate | Art. Nr: 201139 |
|---|---|
| NaVO$_3$ | 121.93 g/mol |
| part of Vanadium | 50.94 g/mol |
| proportion of Vanadium | 41.78% |
| Amount to be co-lyophilised with 100 g KCl | |
| Sodium Metavanadat | 42.36 mg |
| part of Vanadium | 17.70 mg |
| conzentration Vanadium in the resulting co-lyophilisate: | 176.97 µg/g |

| Selenium in Sodiumselenite | Art. Nr: 201140 |
|---|---|
| Na$_2$SeO$_3$ | 172.94 g/mol |
| part of Selenium | 78.96 g/mol |
| proportion of Selenium | 45.66% |
| Amount to be co-lyophilised with 100 g NaCl | |
| Sodiumselenite | 2740.00 mg |
| part of Selenium | 1251.01 mg |
| conzentration Molybdenum in the resulting co-lyophilisate: | 12510.14 µg/g |

| Tin in Tin(II)-chloride × 2H$_2$O | Art. Nr: 201128 |
|---|---|
| SnCl$_2$ × 2H$_2$O | 225.63 g/mol |
| part of Tin | 65.41 g/mol |
| proportion of Tin | 28.99% |
| Amount to be co-lyophilised with 100 g MgSO$_4$ | |
| Tin(II)-chloride × 2H$_2$O | 7.98 mg |
| paet of Tin | 2.31 mg |
| conzentration Tin in the resulting co-lyophilisate: | 23.13 µg/g |

The above co-lyophilisates have been used for the preparation of a chemically defined cell culture media for Chinese hamster ovary cells.

By using the co-lyophilisates the overall amount of the trace element (low-abundant component) still remains the same as outlined in the recipe, but as it is combined with the carrier salt the precision in weighing in a larger amount of substance and the mixing of lyophilisates is significantly higher.

2. Cell Culture Media Production

All ingredients of the medium including the co-lyophilisates are mixed, and milled using a dosage snail and a pin mill. In the dosage snail the ingredients are treated with liquid nitrogen.

The milling is performed under the following conditions:
Temperature—mill: 10° C.
Oxygen level: below 10% absolute
Rpm—Mill: up to 2800 1/min
Blending time: 30 min
Rpm dosage snail: 40 1/min The resulting powdered cell culture medium is suitable for the culture of CHO (Chinese Hamster Ovary) cells.

3. Application Data

The reproducibility in producing a dry powder chemically defined medium with the desired physico-chemical properties and the cellular performance is tested as outlined below in batch growth showing the integral viable cell density (IVCD) over time of CHO S cells in comparison to other media. The media are produced using the pin mill technology using inert conditions.

Alpha CHO (Pilot Lot 1, 2 and 3) being the media produced according to the method of the present invention.

FIG. 1 shows the integrated viable cell density. The other media that are not produced according to the method of the present invention have a different composition but are all dedicated for CHO cells.

Additionally the media performance is tested on volumetric titer expressing a monoclonal antibody.

Figure 2:
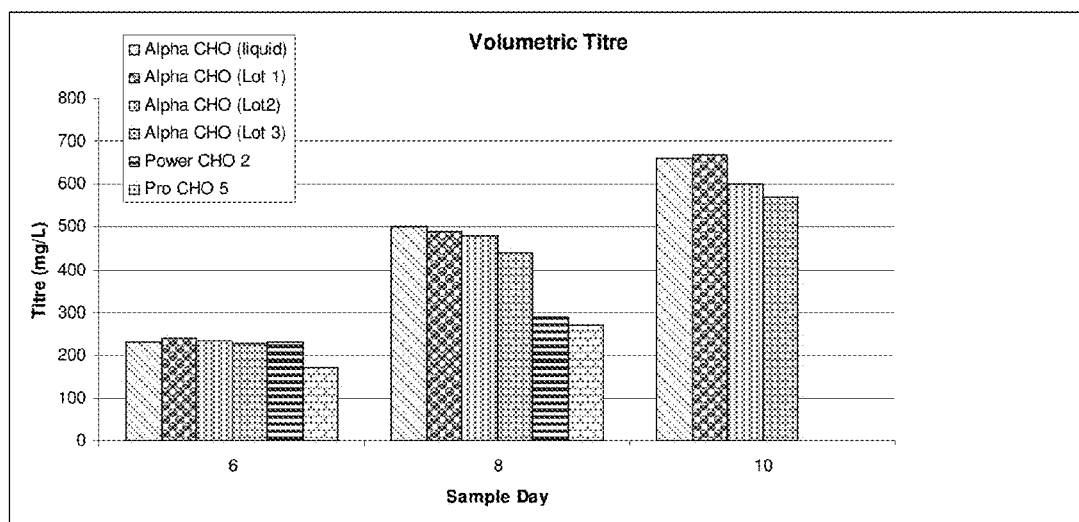
FIG. 2—Is a graph.

FIG. 2 shows the volumetric titer.

Figure 3:
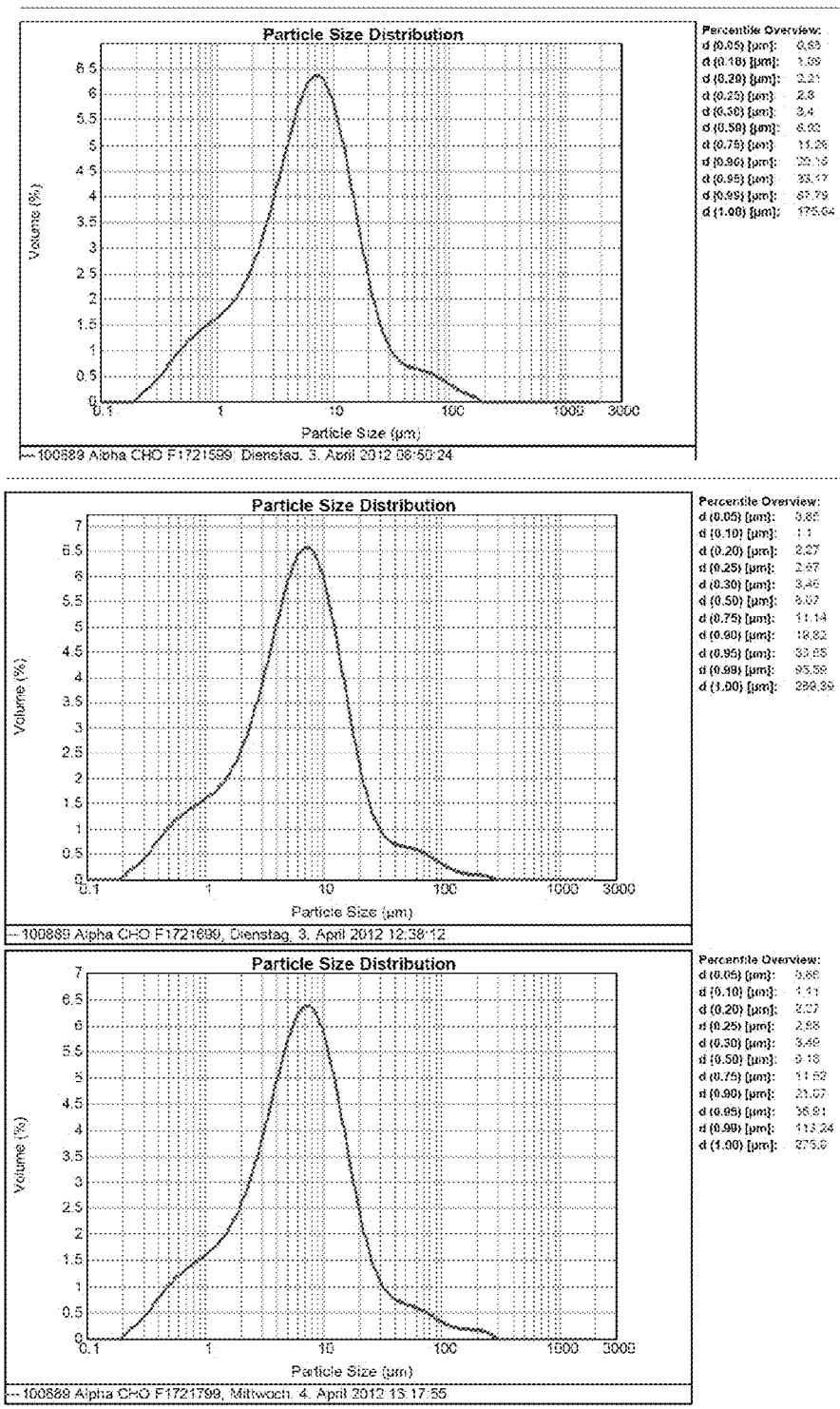
FIG. 3—Is a graph.

For the analysis of batch to batch consistent production of dry powder media besides the cellular testing, particle size distribution of three productions is tested for three independent production batches. FIG. 3 shows the particle size distribution.

The invention claimed is:

1. A process for manufacturing cell culture media by
    a) co-lyophilizing at least two components of a cell culture medium whereby the amount of at least one component, a less abundant component, is less than 5% by weight of the amount of at least one other component, a high abundant component;
    b) mixing one or more co-lyophilisates generated in step a) with one or more other components of the cell culture medium;
    c) subjecting the mixture of step b) to milling.

2. Process according to claim 1 characterized in that the high abundant component is Sodium Chloride (NaCl), Potassium chloride (KCl), Calcium chloride ($CaCl_2$), Magnesium chloride ($MgCl_2$) or Magnesium sulphate ($MgSO_4$).

3. Process according to claim 1, characterized in that in step a) the co-lyophilisation is performed by generating an aqueous solution of the components, freezing the mixture and removing the liquid under reduced pressure.

4. Process according to claim 1, characterized in that the mixture from step b) is milled in a pin mill, fitz mill or a jet mill.

5. Process according to claim 1, characterized in that the mixture resulting from step b) is cooled to a temperature below 0° C. prior to milling.

6. Process according to claim 1, characterized in that in step a) two or more different co-lyophilisates are produced, each by co-lyophilizing at least two components of the cell culture medium.

* * * * *